United States Patent [19]

Gessman

[11] Patent Number: 4,543,963
[45] Date of Patent: Oct. 1, 1985

[54] METHOD AND APPARATUS FOR DIFFERENTIATING ANTEGRADE FROM RETROGRADE P-WAVES AND FOR PREVENTING PACEMAKER GENERATED TACHYCARDIA

[76] Inventor: Lawrence J. Gessman, 1929 West Point Ct., Cherry Hill, N.J. 08003

[21] Appl. No.: 554,179

[22] Filed: Nov. 22, 1983

[51] Int. Cl.⁴ .......................... A61B 5/04; A61N 1/36
[52] U.S. Cl. ................. 128/702; 128/419 PG
[58] Field of Search ................. 128/702, 703, 419 PG

[56] References Cited

U.S. PATENT DOCUMENTS

| | | | |
|---|---|---|---|
| 3,448,739 | 6/1969 | Stark et al. | 128/658 |
| 3,634,924 | 1/1972 | Blake et al. | 264/230 |
| 3,648,707 | 3/1972 | Greatbatch | 128/419 PG |
| 3,746,003 | 7/1973 | Blake et al. | 604/100 |
| 3,833,004 | 9/1974 | Vasquez et al. | 264/230 |
| 3,995,623 | 12/1976 | Blake et al. | 128/419 X |
| 4,088,140 | 5/1978 | Rockland et al. | 128/419 D |
| 4,328,806 | 5/1982 | Cooper | 128/642 |
| 4,329,993 | 5/1982 | Lieber et al. | 128/691 |
| 4,329,994 | 5/1982 | Cooper | 128/672 |
| 4,452,248 | 6/1984 | Keller, Jr. | 128/419 PG |

FOREIGN PATENT DOCUMENTS 2026870 2/1980 United Kingdom ......... 128/419 PG

OTHER PUBLICATIONS

"Transvenous Physiological Pacing-A New Atrioventricular Electrode" by Thomas Z. Lajos, PACE vol. 5, Mar.-Apr. 1982.
"Swan-Ganz Pacing-TD Catheter", Distributed by American Edwards Laboratories, dated Aug. 1982.

Primary Examiner—William E. Kamm
Attorney, Agent, or Firm—Benasutti and Murray

[57] ABSTRACT

An improved dual chamber cardiac pacing apparatus detects retrograde P-waves conduction by either determining polarity of the P-wave at a location in the right atrium adjacent the A-V node; or the sequence of signals which appear at this predetermined location and at a second predetermined location in the atrium in proximity to the sinus node. The pacing apparatus will ignore retrograde P-waves when initiating sequential pacing in the ventricle. In addition, the pacing apparatus will provide a burst of high rate atrial pacing pulses upon detection of the simultaneous occurrence of retrograde P-wave conduction, high rate heart beat and narrow QRS complexes.

33 Claims, 10 Drawing Figures

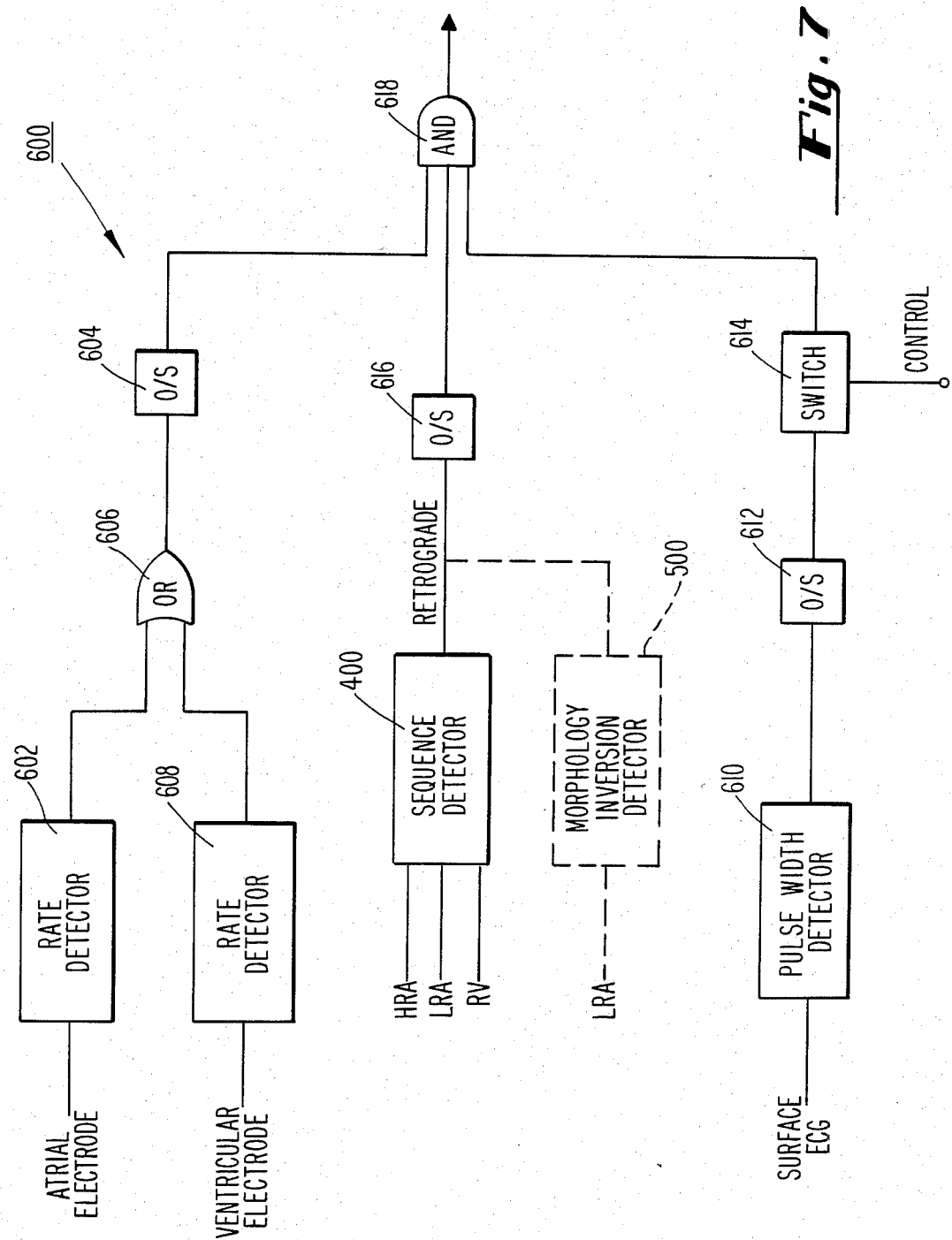

METHOD AND APPARATUS FOR DIFFERENTIATING ANTEGRADE FROM RETROGRADE P-WAVES AND FOR PREVENTING PACEMAKER GENERATED TACHYCARDIA

BACKGROUND OF THE INVENTION

This invention relates to cardiac pacemakers and more particularly to improvements in dual chamber pacing apparatus.

Dual chamber pacemakers are used in those patients suffering from complete heart block and those who can benefit from an increase in ventricular rate and cardiac output in accordance with an increase in physical activity. The typical dual chamber pacemaker essentially comprises dual demand pacers, one for the atrium and one for the ventricle. Each demand pacer includes a sensing element and a pacing element positioned in its respective chamber. Each pacer has an intrinsic escape interval, that is a lower rate limit for the sensed atrial beats. If the time between suceeding atrial beats exceeds the refractory period of the pacer, the pacer will initiate a paced beat. For example, with the pacemaker escape interval set at 0.86 seconds (corresponding approximately to 70 beats per minute), the pacemaker itself will initiate a beat if it does not sense a spontaneous beat within this time period. Consequently, during occurrences of bradycardia or asystole, the pacemaker will output paced beats once every 0.86 seconds, thereby causing the paced chamber to beat at approximately 70 beats per minute.

For dual chamber pacemakers, the pacemaker atrial and ventricular output beats are synchronized. For example, in patients with normal sinus rhythm and heart block, the atrial demand pacemaker functions on a standby basis. That is, it senses the atrial beats but does not generate atrial pacing pulses because of the presence of the sinus beats. Meanwhile, the ventricular sensor awaits a ventricular beat. If the beat is not sensed within a predetermined, artifically induced A-V delay period (typically 200 milliseconds), the ventricular pacing electrode will generate a pacing pulse. As a result, the heart chambers beat in closely approximated natural synchronism.

It has been estimated that at least 45% of all patients who require a pacemaker implant have 1:1 retrograde V-A conduction, including approximately 67% of those with sick sinus syndrome and 14% of those with complete antegrade heart block. This means that in those patients with retrograde V-A conduction, the pulse which stimulates the ventricle is conducted back through the A-V node into the atrium. When this occurs in patients using the dual demand pacemakers, the atrial pacemaker senses this retrograde pulse as an atrial pacing pulse. This triggers the artificial A-V delay causing the ventricular pacing electrode to generate a pulse at the end of the preset 200 millisecond delay period. Because of the retrograde V-A conduction, this pulse will also be conducted back to the atrial sensing electrode causing the cycle to be repeated.

This phenomenon can likely result in pacemaker mediated tachycardia, causing the ventricle to contract every 400 milliseconds. That is, the ventricle pacemaker will output a pacing pulse every 200 milliseconds after an atrial pulse is sensed; and, due to the retrograde V-A conduction of the ventricular pulse, the atrial sensing will occur 200 milliseconds after each pacemaker generated ventricular pacing pulse. This 400 millisecond cycle causes the ventricle to contract approximately 150 times per minute. This phenomenon at best causes much discomfort and anxiety in the pacemaker patient; and, at worst, may cause severe pathological problems. Consequently, it can be seen that an improved dual demand pacemaker, which does not participate in the onset of tachycardia, is highly desirable.

Another anomalous phenomenon exhibited by the human heart is paroxysmal atrial tachycardia (PAT) which results from high rate pacing beats spontaneously generated from a location in the upper portion of the A-V node. PAT can be relieved by application of premature atrial pacing pulses or high rate atrial pacing pulses which are applied in bursts. Consequently, pacemakers are available which measure the atrial beat rate and apply atrial pacing pulses if the measured atrial rate exceeds a predetermined level. The problem with this type of pacemaker is that high atrial beat rates can be caused by other conditions such as ventricular tachycardia in patients having retrograde V-A conduction or under circumstances wherein the atrial pacing rate sensor is actually sensing the ventricular tachycardia waveforms due to a far field effect. In these situations, the application of a burst of high rate atrial pacing pulses would be ineffective. Also, high atrial heat rates can be the result of a normally elevated sinus rate due to physical exertion. In this case, atrial burst pacing is neither necessary nor desirable. Consequently, an improved pacemaker which can uniquely determine the onset of atrial tachycardia is also highly desirable.

SUMMARY OF THE INVENTION

The present invention eliminates the onset of pacemaker mediated tachycardia, by differentiating between antegrade P-waves and retrograde P-waves, and triggering ventricular contraction based upon antegrade P-waves only. In addition, the present invention uniquely determines the onset of paroxysmal atrial tachycardia by detecting the presence of retrograde atrial pacing pulses in conjunction with the presence of an atrial beat rate which exceeds a predetermined level.

The preferred embodiment of the present invention utilizes a pair of P-wave sensors associated with the right atrium. A high right atrial (HRA) sensor, preferably positioned in an upper portion of the right atrium in proximity to the sinus node is physically separated from a low right atrial (LRA) sensor, preferably positioned in a lower portion of the right atrium in proximity to the tricuspid valve and as close to the A-V node as possible. An atrial pacing electrode is preferably positioned in the right atrial appendage and a ventricular pacing electrode is preferably positioned in the right ventricular apex.

If the pacemaker senses a LRA signal before it senses a HRA signal, it inhibits the output of a ventricular pacing signal since this phenomenon is recognized by the pacemaker as a retrograde P-wave. An HRA signal sensed before an LRA signal is recognized as an antegrade P-wave, which alerts the pacemaker to look for a ventricular pacing pulse. If the ventricular pacing pulse does not occur within a predetermined delay period, preferably on the order of 200 milliseconds, the pacemaker will then initiate a ventricular pacing pulse causing the ventricle to contract.

In an alternate embodiment, the morphology of the P-wave detected by the LRA electrodes is used to determine the presence of antegrade or retrograde P-wave conduction.

In addition, if the pacemaker senses an atrial heat rate which exceeds the predetermined level, for example 150 beats per minute in the preferred embodiment, and each beat is recognized as a retrograde P-wave, the pacemaker will initiate premature atrial pacing pulses or a burst of high rate atrial pacing pulses in order to alleviate paroxysmal atrial tachycardia.

It is therefore an overall object of the present invention to provide an improved dual demand pacemaker which will not initiate tachycardia.

It is another object of the present invention to provide an improved dual demand pacemaker which will not generate a pacing pulse based upon retrograde P-wave conduction.

It is a further object of the present invention to provide an improved dual chamber pacemaker which differentiates between antegrade and retrograde P-waves.

Still another object of the present invention is to provide an improved dual chamber pacemaker having dual atrial sensors, one for sensing signals in an upper portion of the atrium and the other for sensing signals in a lower portion of the atrium.

A further object of the present invention is to provide an improved dual demand pacemaker which senses the occurrence of P-waves in the upper and lower portions of the atrium, compares the sequence of occurrence of said signals, then initiates or prevents the production of ventricular pacing pulses based upon the sequential relationship of the high and low atrial signals.

It is yet another object of the present invention to provide an improved dual demand pacemaker which inhibits the output of a ventricular pacing pulse upon the occurrence of a P-wave signal in the lower portion of the atrium before the occurrence of a P-wave signal in the upper portion of the atrium.

It is a further object of the present invention to provide an improved pacemaker which differentiates between antegrade and retrograde P-waves based upon the inversion of morphology of the retrograde relative to antegrade signals sensed in the lower portion of the atrium in proximity to the A-V node.

It is still another object of the present invention to provide an improved pacemaker which uniquely determines the onset of paroxysmal atrial tachycardia.

Another object of the present invention is to provide an improved pacemaker which applies premature atrial pacing pulses or a burst of high rate pacing pulses to the atrium upon detection of retrograde P-waves which occur at a rate exceeding a predetermined level.

These and other objects of the present invention will become apparent from the following more detailed description.

BRIEF DESCRIPTION OF THE DRAWING

The present invention may be more readily understood by reference to the accompanying drawing in which:

FIG. 7 is a block diagram depicting a PAT detection circuit in accordance with the present invention.

DETAILED DESCRIPTION OF THE PREFERRED EMBODIMENT

Figure 1:
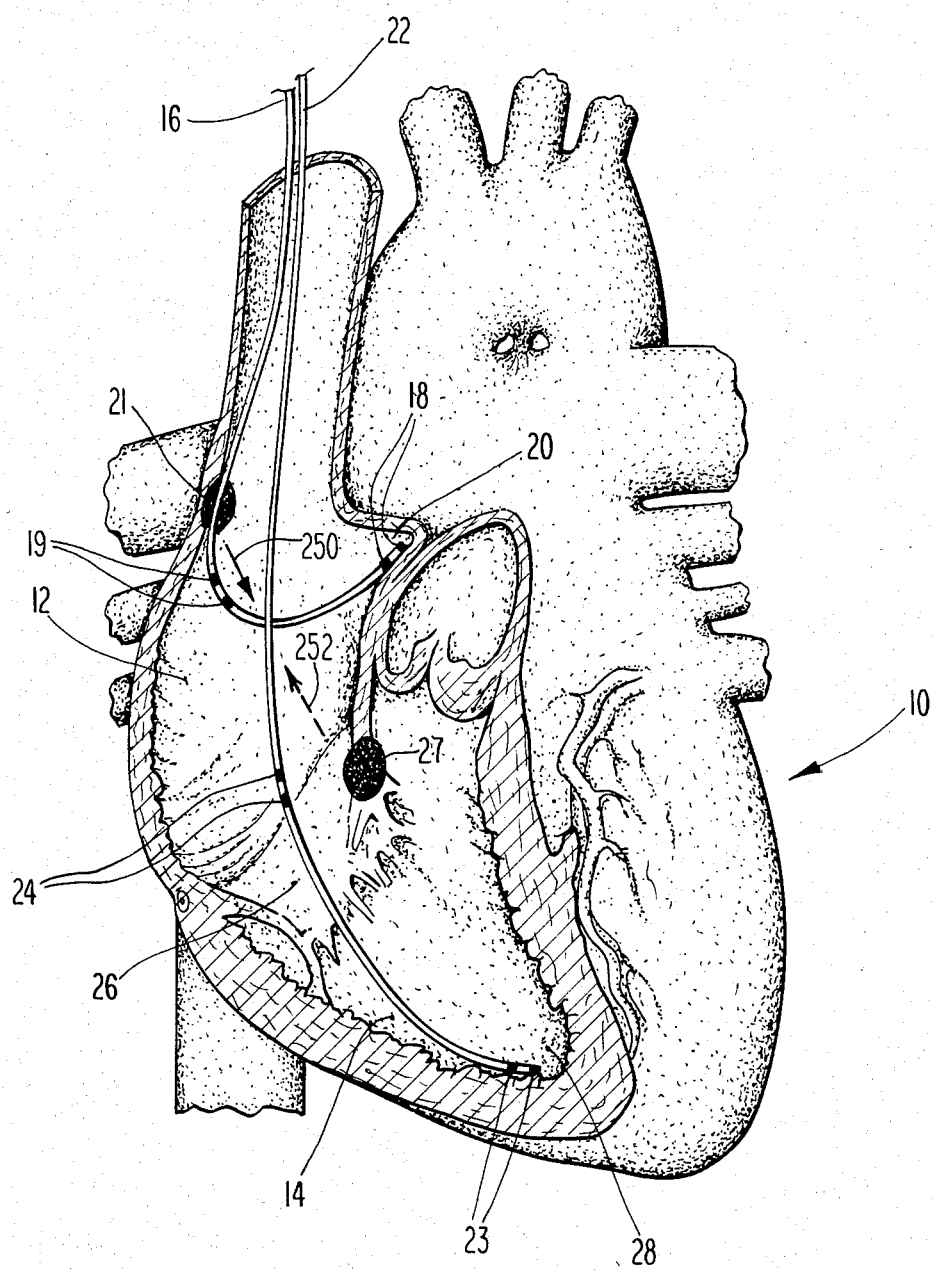
FIG. 1 is a view of the human heart, sectioned through the right atrium and right ventricle, showing the preferred position of pacemaker electrodes in accordance with the present invention.

Referring to FIG. 1 there is shown a pictorial representation of a human heart generally designated 10, depicting a sectional view of the right atrium 12 and the right ventricle 14. A first catheter 16, having a pair of atrial pacing electrodes 18 and a pair of high right atrial (HRA) sensing electrodes 19 is inserted into the right atrium 12 preferably by transvenous implantation. The atrial pacing electrodes 18 are preferably positioned within the atrial appendage 20. The HRA electrodes 19 are preferably positioned in proximity to the sinus node 21. A second catheter 22, having a pair of ventricular pacing electrodes 23 and a pair of low right atrial (LRA) sensing electrodes 24 is also inserted into the right atrium 12 preferably by transvenous implantation. The LRA sensing electrodes 24 are preferably positioned just above and in proximity to the tricuspid valve 26, as close to the A-V node 27 as practical. The ventricular pacing electrodes 23 are preferably positioned in the right ventricular apex 28.

In the preferred embodiment, the HRA electrodes 19, the LRA electrodes 24, the atrial pacing electrodes 18 and the ventricular pacing electrodes 23 each comprise a bipolar electrode pair. The distance between the two electrodes of each bipolar pair is preferably in the range of one to ten millimeters. The ventricular pacing electrodes 23 are preferably positioned at the distal end of the catheter 22, with the LRA electrodes 24 being set back approximately eleven centimeters. Note that this dimension varies in accordance with the size of the heart as will be discussed hereinafter, however, the fundamental requirement is that the LRA electrodes 24 be located in proximity to the A-V node 27 on the atrial side of the valve when the distal end of the catheter 22 is positioned in the ventricular apex 28. The atrial pacing electrodes 18 are preferably positioned at the distal end of catheter 16, with the HRA electrodes 19 being set back a distance such that the HRA electrodes 19 are in proximity to the sinus node 21 when the atrial pacing electrodes 18 have been positioned within the atrial appendage 20.

Although FIG. 1 depicts electrodes which have been transvenously inserted into the right chambers of the heart, it is within the scope and contemplation of the present invention that these electrodes may also be implanted surgically via thoracotomy; or into the mediastinal contents surrounding the right chambers via mediastinoscopy. In addition, although the preferred embodiment depicts bipolar electrode pairs, it is also within the scope and contemplation of the present invention to substitute unipolar electrodes or orthogonal bipolar electrode pairs for any one or more of the bipolar electrode pairs.

Referring now to FIG. 2, there is shown four alternate embodiments of electrodes for use with the apparatus of the present invention. In FIG. 2a, there is depicted a first, hexapolar catheter 200 having a pair of HRA sensing electrodes 202, a pair of LRA sensing electrodes 204, and a pair of ventricular pacing electrodes 206. The ventricular pacing electrodes 206 are preferably disposed at the distal end of catheter 200, with the LRA sensing electrodes 204 being set back approximately eleven centimeters therefrom, and the HRA sensing electrodes 202 being set back approximately 14 centimeters from the distal electrodes 206. The first electrode 200 is inserted into the right chambers of the heart, preferably by transvenous insertion, with the ventricular pacing electrodes 206 being positioned within the ventricular apex, the LRA sensing electrodes 204 being positioned in proximity to the tricuspid valve 26, as close to the A-V node 27 as practical. The HRA sensing electrodes 202 are placed in proximity to the sinus node 21. A second catheter 208, having a pair of atrial pacing electrodes 210 disposed at the distal end thereof, is inserted into the right atrium with the atrial pacing electrodes 210 preferably being positioned within the atrial appendage. If atrial pacing is not indicated, the second catheter 208 is not required. In necessary, either one of the atrial electrode pairs 202 or 204 can be used for atrial pacing.

Figure 2A:
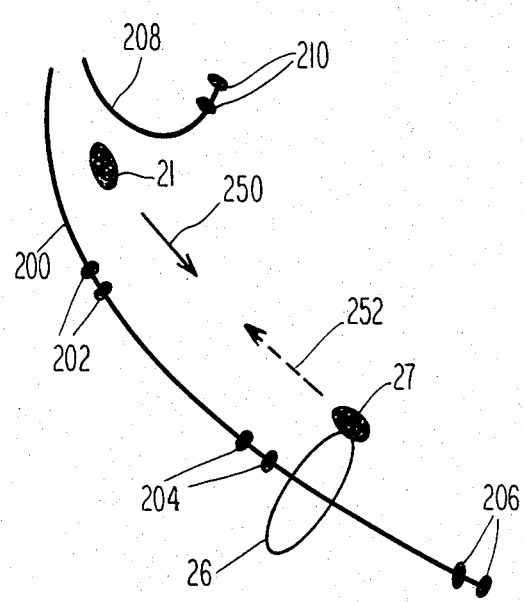
FIGS. 2a to 2d are schematic representations of the relative placement within the heart chambers of four alternate electrode configurations in accordance with the present invention.
Figure 2B:
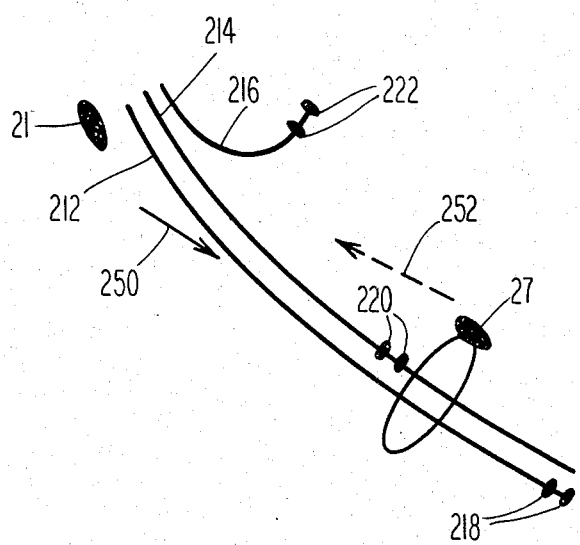

FIG. 2b detects another alternate embodiment of electrodes for use with the apparatus of the present invention. This alternate embodiment utilizes a first catheter 212, a second catheter 214 and a third catheter 216. The first catheter 212 comprises a pair of ventricular pacing electrodes 218 at the distal end thereof. This catheter is inserted into the right ventricle such that the ventricular pacing electrodes 218 are positioned in the right ventricular apex. The second catheter 214 includes a pair of LRA electrodes 220, set back from the distal end of the catheter such that when the catheter 214 is inserted into the right chambers of the heart, with the distal end being positioned in the ventricular apex, the LRA electrodes 220 are positioned adjacent the tricuspid valve 26 as close to the A-V node 27 is practical. The third catheter 216 comprises a pair of atrial pacing electrodes 222 at the distal end thereof. The third catheter 216 is inserted into the right atrium with the atrial pacing electrodes 222 being positioned within the atrial appendage. This embodiment, employing LRA electrodes only, can be used in that embodiment of the present invention which senses morphology of the P-waves to determine antegrade or retrograde conduction as will be described hereinafter. Again, the third catheter 216 is not required if atrial pacing is not indicated; and, if necessary, atrial pacing can be implemented using the LRA electrodes 220.

Figure 2C:
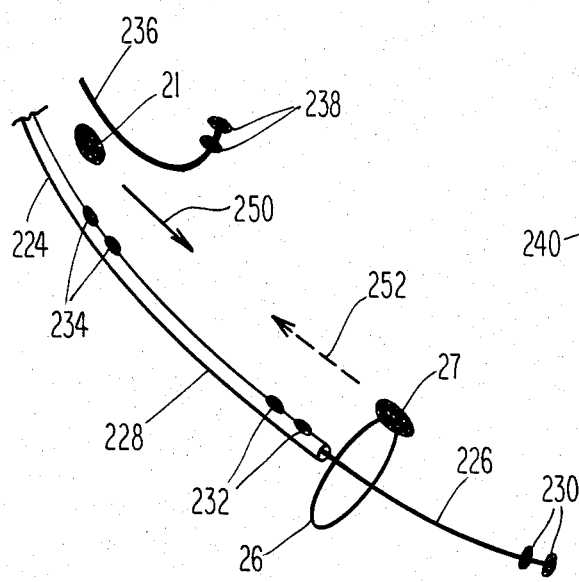

FIG. 2c shows yet another alternate embodiment of electrodes for use with the present invention. This embodiment comprises a first catheter 224 having an inner catheter 226 disposed within the lumen of a hollow outer catheter 228. The inner catheter 226 has a pair of ventricular pacing electrodes 230 disposed at the distal end thereof. The outer catheter 228 includes a pair of LRA electrodes 232 disposed adjacent the distal end thereof and a pair of HRA electrodes 234 set back a predetermined distance from the LRA electrodes, approximately three centimeters in the preferred embodiment. This electrode catheter configuration is designed to accommodate the variation in distances between the ventricular pacing electrodes and the LRA electrodes necessitated by differences in the sizes of human hearts. The inner electrode 226 slides within the outer electrode 228 which enables the distance between the ventricular pacing electrodes 230 and the LRA electrodes 223 to be varied. To use, the surgeon would insert the catheter 224 into the right chambers of the heart, preferably using transvenous insertion techniques in conjunction with fluoroscopy, until the ventricular pacing electrodes 230 were positioned within the ventricular apex. The outer electrode 228 would then be withdrawn until the LRA electrodes 232 were positioned as close to the A-V node 27 as possible. At this point, the outer electrode could be secured to the inner electrode, for example by crimping, in order to maintain the spacial relationship between the ventricular pacing electrodes 230 and the LRA electrodes 232. In addition to the first catheter 224, a second catheter 236 having a pair of atrial pacing electrodes 238 disposed at the distal end thereof, may be inserted into the right atrium with the atrial pacing electrodes 238 positioned within the atrial appendage. Once again, the catheter 236 is not required if atrial pacing is not indicated; and, if necessary, atrial pacing can be implemented using either the HRA or LRA electrode pairs, 234 and 232 respectively.

Figure 2D:
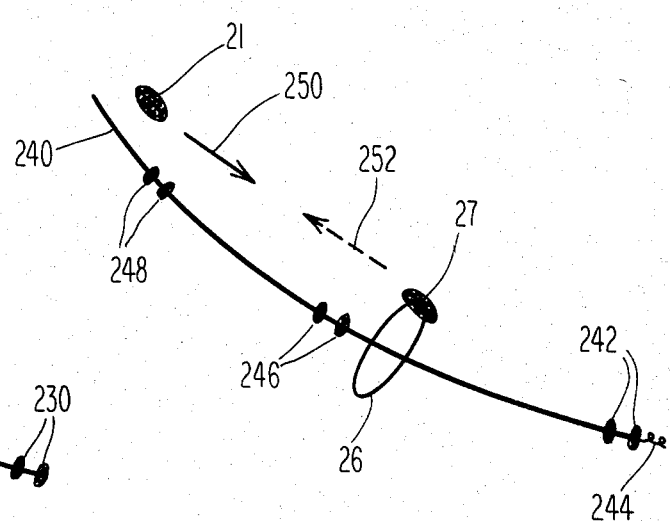

Still another alternate embodiment of electrode configuration for use with the present invention is shown in FIG. 2d. This embodiment comprises a single hexapolar catheter 240 having a pair of ventricular pacing electrodes 242 disposed adjacent the distal end thereof. A small pig tail screw-in anchor 244 is disposed at the distal end of the catheter 240. A pair of LRA electrodes 246 is set back from the ventricular pacing electrodes 242, for a distance of approximately eleven centimeters in the preferred embodiment. A pair of HRA sensing electrodes 248 is set back from the LRA sensing electrodes 246 for a distance of approximately three centimeters in the preferred embodiment. To use, the surgeon inserts the catheter 240 into the heart and screws the pig tail anchor 244 into the myocardium at the ventricular apex. The catheter 240 is then pulled back which causes the LRA electrodes to be drawn toward the A-V node 27 due to the shape of the heart chambers, as can be seen more clearly in FIG. 1. As shown in FIG. 1, with the distal end of the catheter anchored into the ventricular apex, as the catheter is withdrawn, the curvature of the catheter tends to straighten out causing the LRA electrodes 24 to move toward the A-V node 27.

Figure 3:
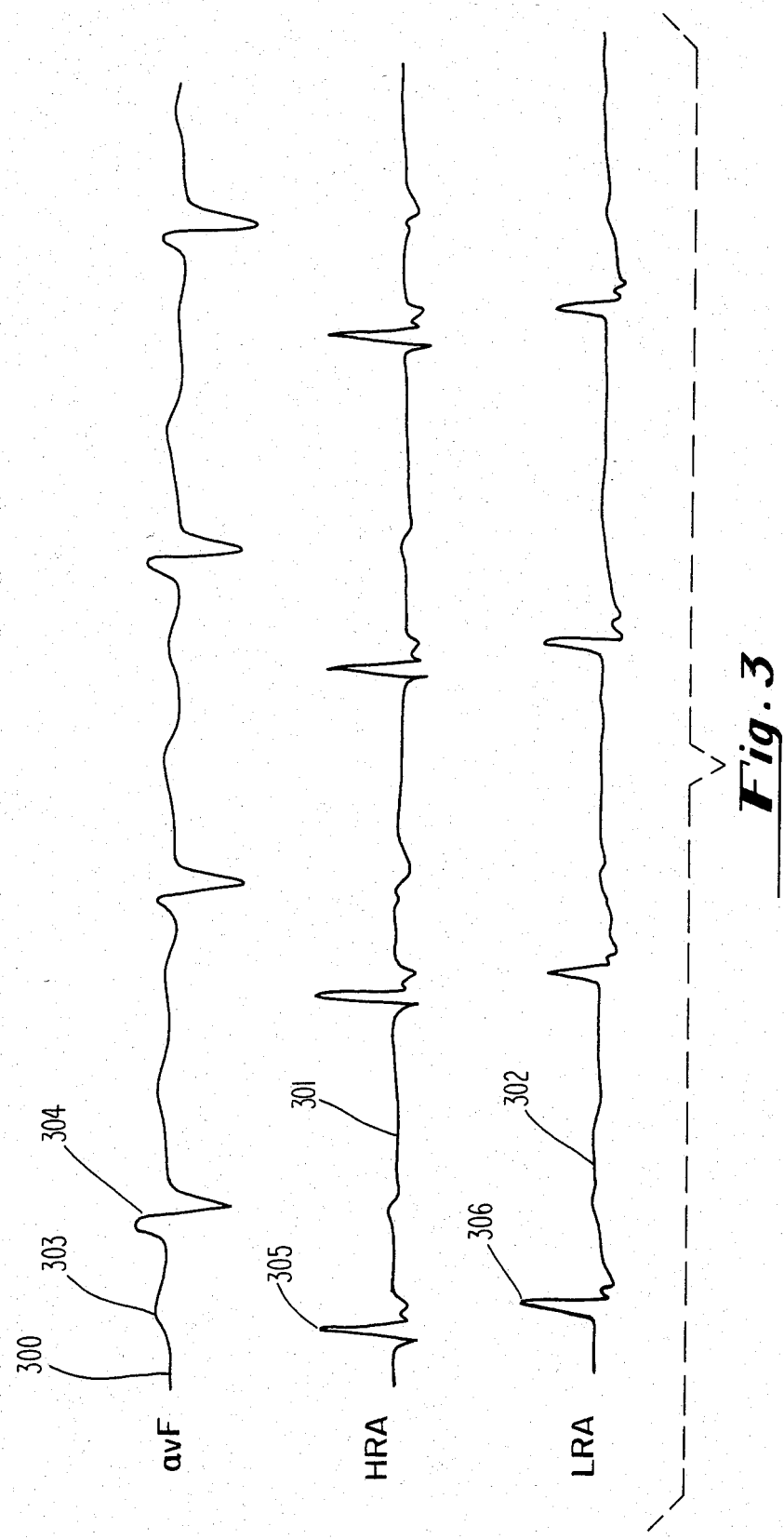
FIG. 3 diagrammatically depicts the timing sequence of electrocardiogram signals as well as high right atrial and low right atrial signals showing the sequence of occurrence of the atrial signals associated with antegrade P-wave condition.

Referring to FIG. 3, there are shown three diagrammatic electrocardiogram waveforms in timed relationship. The top waveform 300 is the diagrammatic representation of an electrocardiogram of a heart in sinus rhythm taken across skin sensors attached to the wrist and ankle. Directly beneath that is the waveform 301 of the signal sensed at the HRA electrode pair 18 and beneath that is the waveform 302 of the signal sensed at the LRA electrode pair 20. The top waveform 300 shows the P-wave 303 which preceeds the QRS complex 304. The elapsed time between the occurrence of the P-wave 303 and the QRS complex 304 is typically on the order of 200 milliseconds when the heart is beating in sinus rhythm. The timed relationship of the HRA waveform 301 and the LRA waveform 302 show that the HRA sensed signal 305 preceeds the LRA sensed signal 306. It has been discovered that the relationship wherein the HRA sensed signal preceeds the LRA sensed signal is indicative of an antegrade P-wave. That is, a P-wave which is conducted from the sinus node to the A-V node generally in the direction indicated by the solid arrows 250 in FIGS. 1 and 2. In measurements made on seven patients, it was found that the HRA sensed signal 305 preceeded the LRA sensed signal 306 by an average of 21 milliseconds (range 10-30 milliseconds) during sinus rhythm in antegrade conduction.

Figure 4:
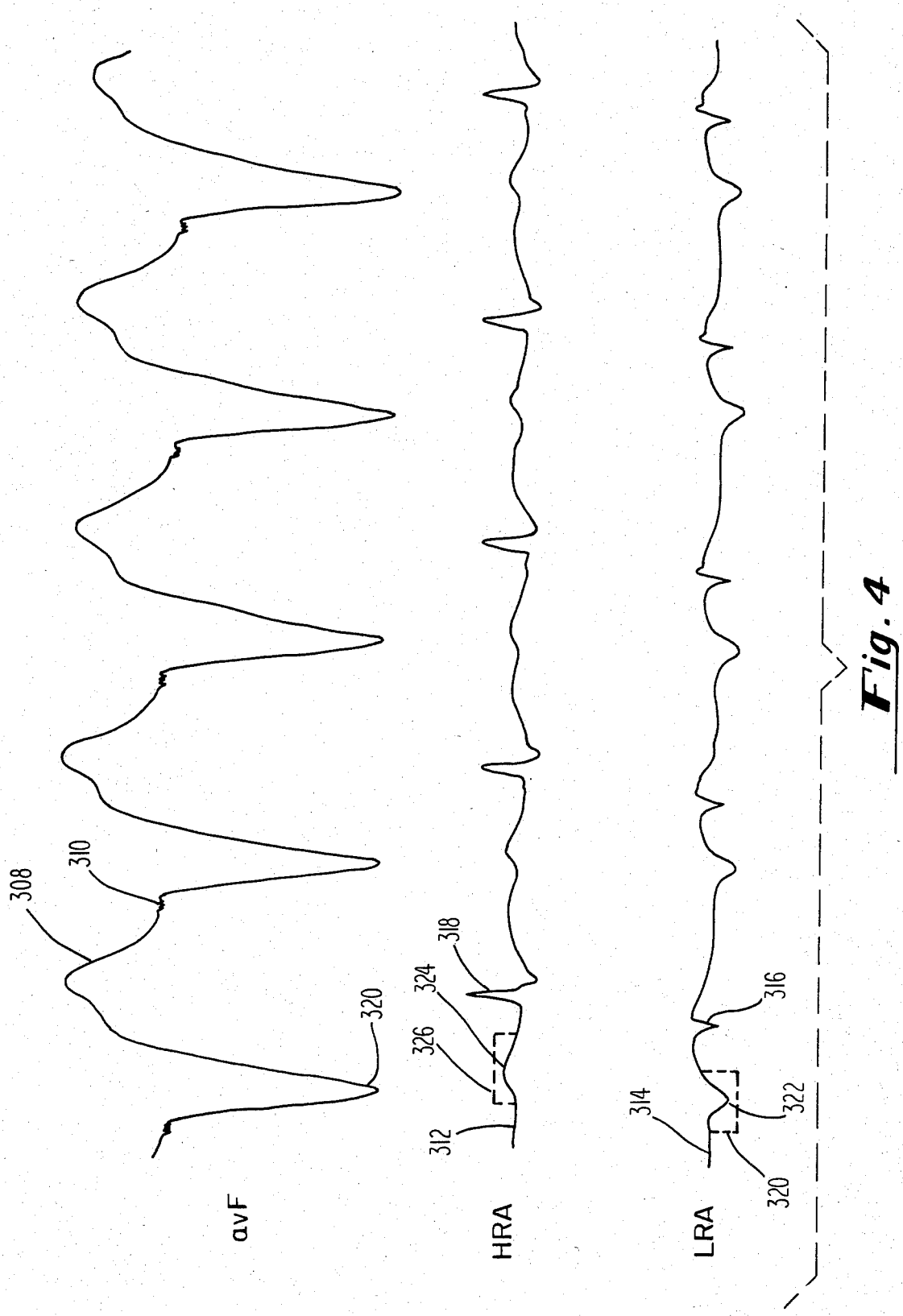
FIG. 4 diagrammatically depicts the timing sequence of electrocardiogram signals as well as high right atrial and low right atrial signals showing the sequence of occurrence of the atrial signals associated with retrograde P-wave conduction as well as the impact of large ventricular QRS waveform on the atrial waveforms due to far field effect.

Referring to FIG. 4, there are shown three electrocardiogram waveforms in timed relationship. The top waveform 308 is the diagrammatic representation of an electrocardiogram of a heart undergoing ventricular pacing taken across skin sensors attached to the wrist and ankle. The waveform 308 includes ventricular pacing artifacts 310. Comparing this waveform with waveform 300 of FIG. 3, it can be seen that ventricular pacing typically causes a QRS complex which is greater in amplitude and duration than that measured during sinus rhythm. Referring again to FIG. 4, the middle waveform 312 represents the signal sensed at the HRA electrode pair 18. The lower waveform 314 represents the signal sensed at the LRA electrode pair 20. As can be seen by comparing the middle and lower waveforms, 312 and 314, the P-wave 316 sensed by the LRA electrode pair 20 preceeds the P-wave 318 sensed by the HRA electrode pair 18. During ventricular pacing at 100 beats per minute with 1:1 retrograde V-A conduction; that is, each ventricular pacing beat is conducted from the ventrical to the atrium through the A-V node, the LRA sensed signal preceeded the HRA sensed signal by an average of 23 milliseconds (range 10-30) in measurements taken on seven patients. It has thus been discovered that the relationship wherein the LRA signal preceeds the HRA signal is indicative of a retrograde P-wave. That is, a P-wave which is conducted from the A-V node 27 toward the sinus node 21 generally in the direction indicated by broken arrows 252 in FIGS. 1 and 2.

It can also be seen, by comparing the lower 314 waveform in FIG. 4 with the lower waveform 302 shown in FIG. 3, the P-wave sensed by the LRA electrode pair during retrograde activation has the opposite polarity and inverted morphology as that sensed by the LRA electrode pair during sinus activation. This morphology inversion was found in five of the seven patients examined. It is believed that the closer the LRA sensor is to the A-V node, the more prevalent this measured morphology inversion will become. Consequently, it has also been discovered that in those patients exhibiting this morphology inversion of the LRA sensed signal, it can be a reliable indicator of the presence of the retrograde P-wave conduction.

When the retrograde P-wave is initiated by a QRS complex in the ventricle, it takes approximately 200 milliseconds for the retrograde P-wave to cross the A-V node, in the direction from the ventricle to the atrium, and proceed to a point approximately medial between the AV node and the sinus node. As previously stated, prior art pacemakers sense the presence of the retrograde P-wave, then cause the ventricular pacing electrode to emit a pacing pulse if a QRS complex is not detected by the end of the simulated A-V nodal delay period. This would cause another retrograde P-wave to be conducted back into the atrium where it would in turn be sensed by the atrial sensor. Since the delay across the A-V node is approximately 200 milliseconds, the pacemaker will generate a ventricular pacing pulse every 400 milliseconds or 150 beats per minute and will continue to generate the pacing pulses at this rate until the cycle is broken.

In the present invention, a sensing sequence which senses an LRA signal before an HRA signal indicates a retrograde P-wave which is disregarded by the pacemaker. If the pacemaker senses the P-wave at the HRA electrode pairs prior to the LRA electrode pairs, the pacemaker treats this as an antegrade P-wave and generates a ventricular pacing pulse if a spontaneous pulse was not sensed within the 200 millisecond simulated A-V delay period.

Figure 5:
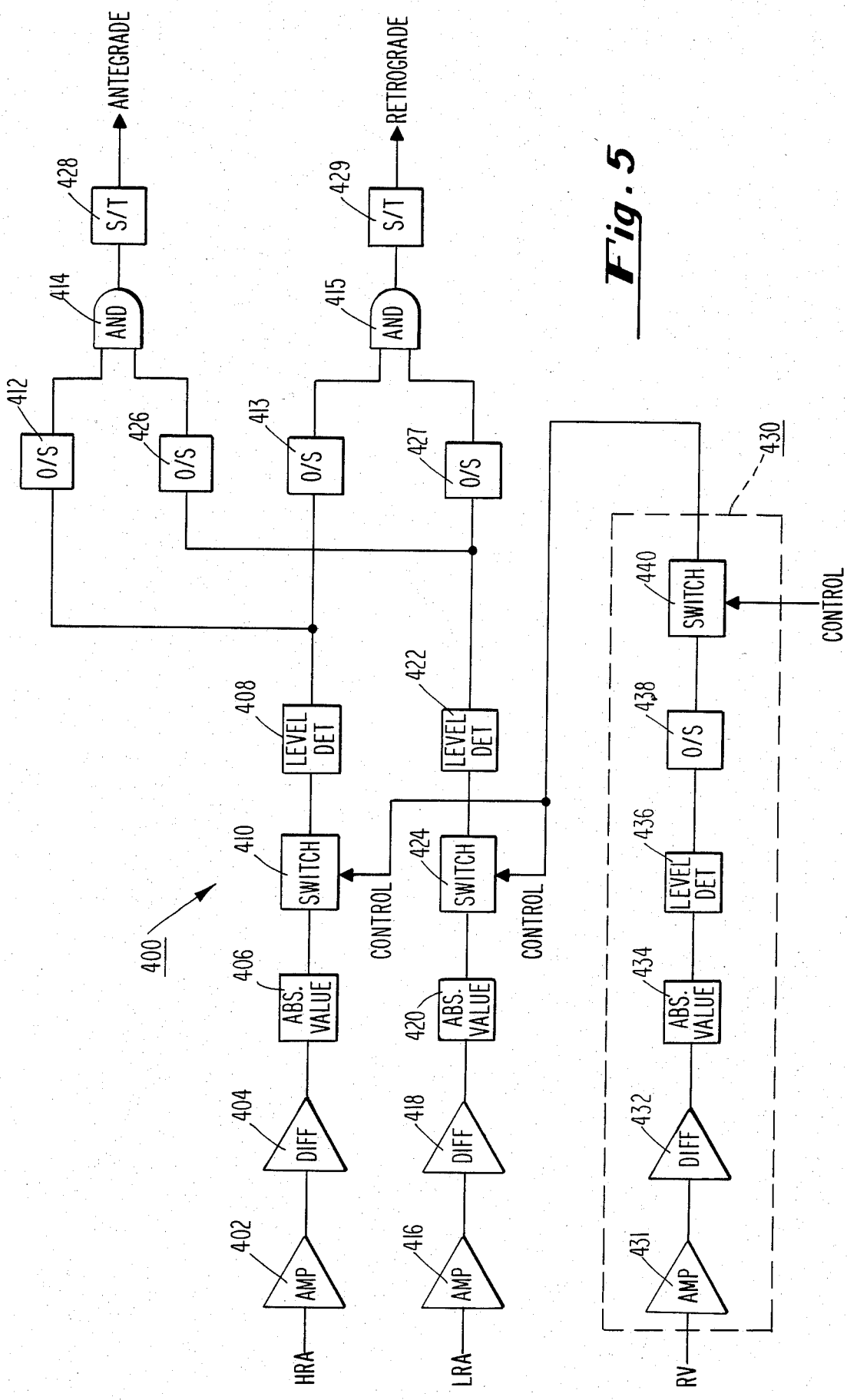
FIG. 5 is a block diagram depicting a P-wave timing sequence detection circuit in accordance with the present invention.

Referring to FIG. 5, there is shown a schematic block diagram of a circuit for detecting the timing sequence between a signal sensed by the HRA electrodes and a signal sensed by the LRA electrodes. The sequence detection circuit, generally designated 400, comprises a first amplifier 402 which receives the signal sensed at the HRA electrodes. In the preferred embodiment, amplifier 402 incorporates band-pass filtering, amplifying those signals whose frequencies are preferably in the range of 5-100 Hz in order to eliminate unwanted signal components such as baseline shifts, T-waves, artifacts and noise.

The amplified and filtered HRA signal appears at the output of the first amplifier 402 which is electrically connected to the input of a differentiator 404. The differentiator 404 sharpens the leading edges of the amplified HRA signal and transmits this signal to an absolute value amplifier 406. The absolute value amplifier 406 converts the HRA waveform to a signal having a single polarity. This signal is input to a first level detector 408 through a first high impedance switch 410, for example a field effect transistor (FET) switch. The first level detector 408 generates an output signal whenever the voltage of the signal from the switch 410 exceeds a predetermined level.

The output of the level detector 408 is applied to the input of a first one shot 412 and the input of a second one shot 413. A signal applied to the input of the first one shot 412 causes it to generate an output pulse having a predetermined pulse width, for example fifty milliseconds in the preferred embodiment. This output pulse is applied to one input of a first two input AND gate 414. A signal applied to the input of the second one shot 413 causes it to generate an output having a predetermined pulse width, for example one millisecond in the preferred embodiment. This output pulse is applied to one input of a second two input AND gate 415.

The signal sensed at the LRA electrodes is applied to the input of a second amplifier 416. The second amplifier 416, like the first amplifier 402, also preferably incorporates band-pass filtering preferably in the range of 5-100 Hz. The output of the second amplifier 416 is applied to the input of a second differentiator 418. The output of the second differentiator 418 is applied to the input of a second absolute value amplifier 420. The output of the second absolute amplifier 420 is applied to the input of a second level detector 422 through a second high impedance switch, for example an FET switch 424. The second level detector 422 produces an output signal when the input from the second absolute value amplifier 420 exceeds a predetermined voltage reference level.

The output of the second level detector 422 is applied to the input of a third one shot 426 and the input of a fourth one shot 427. Upon application of an input signal from the level detector 422, the third one shot 426 will generate an output pulse having a predetermined pulse width, for example one millisecond in the preferred embodiment. This output is connected to the other input of the first two input AND gate 414. A signal applied to the input of the fourth one shot 427 causes it to generate an output pulse having a predetermined pulse width, for example fifty milliseconds in the preferred embodiment. This output pulse is applied to the other input of the second two input AND gate 415. The first 412, second 413, third 426 and fourth 427 one shots each have a predetermined refractory period, for example 100 milliseconds. As a result, once the one shot is triggered, by its associated level detector 408 and 422, it cannot be retriggered until the expiration of the refractory period which is 100 milliseconds in the preferred embodiment.

The output of the first AND gate 414 is applied to an input of a first schmitt trigger 428. The first AND gate 414 will generate an output signal upon full coincidence, that is for at least one millisecond in the preferred embodiment, of output signals from the first and third one shots 412 and 426. Upon receipt of this output signal from the first AND gate 414, the first schmitt trigger 428 generates a first trigger signal. The output of the second AND gate 415 is applied to an input of a second schmitt trigger 429. The second AND gate 415 will generate an output upon full coincidence, that is for at least one millisecond in the preferred embodiment, of output signals from the second 413 and fourth 427. Receipt of this output from the second AND gate 415 causes the schmitt trigger to generate a second trigger signal.

The sequence detection circuit 400 preferably includes a controllable blanking circuit portion shown within the dotted line and generally designated 430 in FIG. 5. The blanking circuit portion 430 receives an RV signal, representative of the QRS complex sensed in the ventricle. The RV signal is applied to a third amplifier 431. The third amplifier 431, like the first and second amplifiers, 402 and 416, preferably incorporates band-pass filtering preferably in the range of 5-100 Hz. The output of the third amplifier 431 is applied to the input of a third differentiator 432. The output of the third differentiator 432 is applied to the input of a third absolute value amplifier 434. The output of the third absolute value amplifier 434 is applied to the input of a third level detector 436. The third level detector 436 generates an output signal when the input signal voltage exceeds a predetermined voltage reference level.

The output of the third level detector 436 is applied to the input of a fifth one shot 438. Upon application of a signal to its input, the fifth one shot 438 will generate an output pulse having a predetermined pulse width, for example 120 milliseconds in the preferred embodiment. This output is applied to the control inputs of the first 410 and second 424 FET switches through a third high impedance switch 440, opening these switches for the duration of the output pulse generated by the fifth one shot 438 when the third switch 440 is conducting. The third high impedance switch 440 is preferably a field effect transistor (FET) switch and is operable by a programmable control which is set when blanking is desired.

The sequence detection circuit 400 operates as follows. After filtering, amplification and shaping by the first amplifier 402, first differentiator 404, and first absolute value amplifier 406, the HRA signal is applied to the input of the level detector 408, assuming the first switch 410 is closed. When the signal exceeds the predetermined reference voltage level which is preferably adjustable to prevent triggering based upon unwanted low level signals, such as noise, T-waves, or far field effects from ventricular contractions, the level detector triggers the first 412 and second 413 one shots. The first one shot 412 generates a fifty millisecond output pulse and the second one shot 413 generates a one millisecond output pulse. Similarly, after filtering, amplification and shaping by the second amplifier 416, second differentiator 418 and second absolute value amplifier 420, the LRA signal is applied to the input of the second level detector 422, assuming the second switch 424 is closed. If this signal exceeds the predetermined reference voltage level which is also preferably adjustable to prevent triggering based upon unwanted low level signals, the second level detector 422 outputs a signal which triggers the third 426 and fourth 427 one shots. The third one shot 426 generates a one millisecond output pulse and the fourth one shot generates a fifty millisecond output pulse.

As previously stated, the first two input AND gate 414 will provide an output signal upon full coincidence of the outputs from the first one shot 412 of the third one shot 426. Consequently, due to the difference in pulse width durations, as well as the time of occurrence, there will be full coincidence of the outputs only if the output of the third one shot 426 (which, as previously stated, represents the occurrence of a signal sensed at the LRA electrodes and is one millisecond in duration) occurs at the same time as the output of the first one shot 412 (which, as previously stated, represents the occurrence of a signal sensed by the HRA electrodes and is fifty milliseconds in duration) or within approximately forty-nine milliseconds after the occurrence thereof (the width of the output pulse of the first one shot 412 less the width of the output pulse of the third one shot 426). As a result, there will be a first trigger signal output from the first schmitt trigger 428 only if the LRA signal is sensed within forty-nine milliseconds following the sensing of the signal at the HRA electrodes. This is ample time since, as previously stated, the range between occurrence of the HRA and LRA signals was measured to be 10-30 milliseconds.

If the LRA signal occurs before the HRA signal, there will be no full coincidence and consequently no output from the first AND gate 414 and no first trigger signal from the first schmitt trigger 428. Therefore, the generation of a first trigger signal is indicative of the occurrence of an HRA signal which occurs before the LRA signal and signifies an antegrade P-wave. This first trigger signal from the first schmitt trigger 428 is applied to the pacemaker A-V nodal delay circuit which, as previously described, will then cause the generation of a ventricular pacing pulse if a spontaneous ventricular pacing pulse has not been sensed within the preset delay period.

The second two input AND gate 415 will provide an output signal upon full coincidence of the outputs from the second one shot 413 and the fourth one shot 427. Consequently, due to the difference in pulse width durations, as well as the time of occurrence, there will be coincidence of the outputs only if the output of the second one shot 413 (which, as previously stated, represents the occurrence of a signal sensed at the HRA electrodes and is one millisecond in duration) occurs at the same time as the output of the fourth one shot 427 (which, as previously stated, represents the occurrence of a signal sensed by the LRA electrodes and is fifty milliseconds in duration) or within approximately forty-nine milliseconds after the occurrence thereof (the width of the output pulse from the fourth one shot 427 less the width of the output pulse of the second one shot 413). As a result, there will be a trigger output from the second schmitt trigger 429 only if the HRA signal is sensed within forty-nine milliseconds following the sensing of the signal at the LRA electrodes. This is ample time since, as previously stated, the range between occurrence of the LRA and HRA signals was measured to be 10–30 milliseconds.

If the HRA signal occurs before the LRA signal, there will be no full coincidence and consequently no output from the second AND gate 414 and no second trigger signal from the second schmitt trigger 429. Therefore, the generation of a second trigger signal is indicative of the occurrence of an LRA signal which occurs before the HRA signal and signifies a retrograde P-wave. This second trigger signal is utilized by the pacemaker of the present invention to alleviate paroxysmal atrial tachycardia as will be subsequently described.

As can be seen referring to FIG. 4, by comparing the HRA and LRA waveforms, 312 and 314, with the electrocardiogram waveform 308, there is a significant amount of cross talk therebetween, especially in the waveform sensed by the LRA electrodes. As shown in FIG. 4, the signal represented by the large negative excursion 320 of the QSR complex 308 is picked up at 322 in the LRA waveform and 324 in the HRA wave form. These could possibly cause an undesired triggering of the HRA and/or LRA detection circuits. To prevent this, the sequence detection circuit 400 preferably includes the blanking circuit portion 430, controlled by FET switch 440, which operates as follows.

As shown in FIG. 5, the QRS signal, indicated by RV, is filtered, amplified, shaped and applied to the input of the third level detector 436. When this signal exceeds the predetermined reference level adjustable to prevent triggering on unwanted low level signals, the third level detector 436 generates an output signal to the fifth one shot 438 which generates an output pulse having a predetermined pulse width, preferably 120 milliseconds in duration. It is preferred that blanking be optional, depending upon the desires of the using physician. If the physician desires to utilize the blanking feature, he closes the third FET switch 440 by setting the appropriate programmable control. The output of the fifth one shot 438, which is a pulse of 120 milliseconds in duration, is then applied to the control inputs of the first and second FET switches 410 and 424. Consequently, first 410 and second 424 switches remain open for 120 milliseconds following the initiation of the QRS complex thereby preventing the application of a signal to the first and second level detectors 408 and 422 during this interval. Therefore, this portion of the sequence detection circuit effectively blanks out those segments of the HRA and LRA waveforms which contain QRS induced excursions. This blanking is represented by the dashed line boxes 326 and 328 in FIG. 4. Consequently, by employing the blanking feature, the circuit of the preferred embodiment will trigger only upon detection of P-waves occurring in the atrium and not those induced by the ventricular QRS complex. The need for blanking may be minimized by the use of orthogonal, bipolar sensing electrodes which are positioned circumferentially around the catheter body, instead of longitudinally along the catheter.

Figure 6:
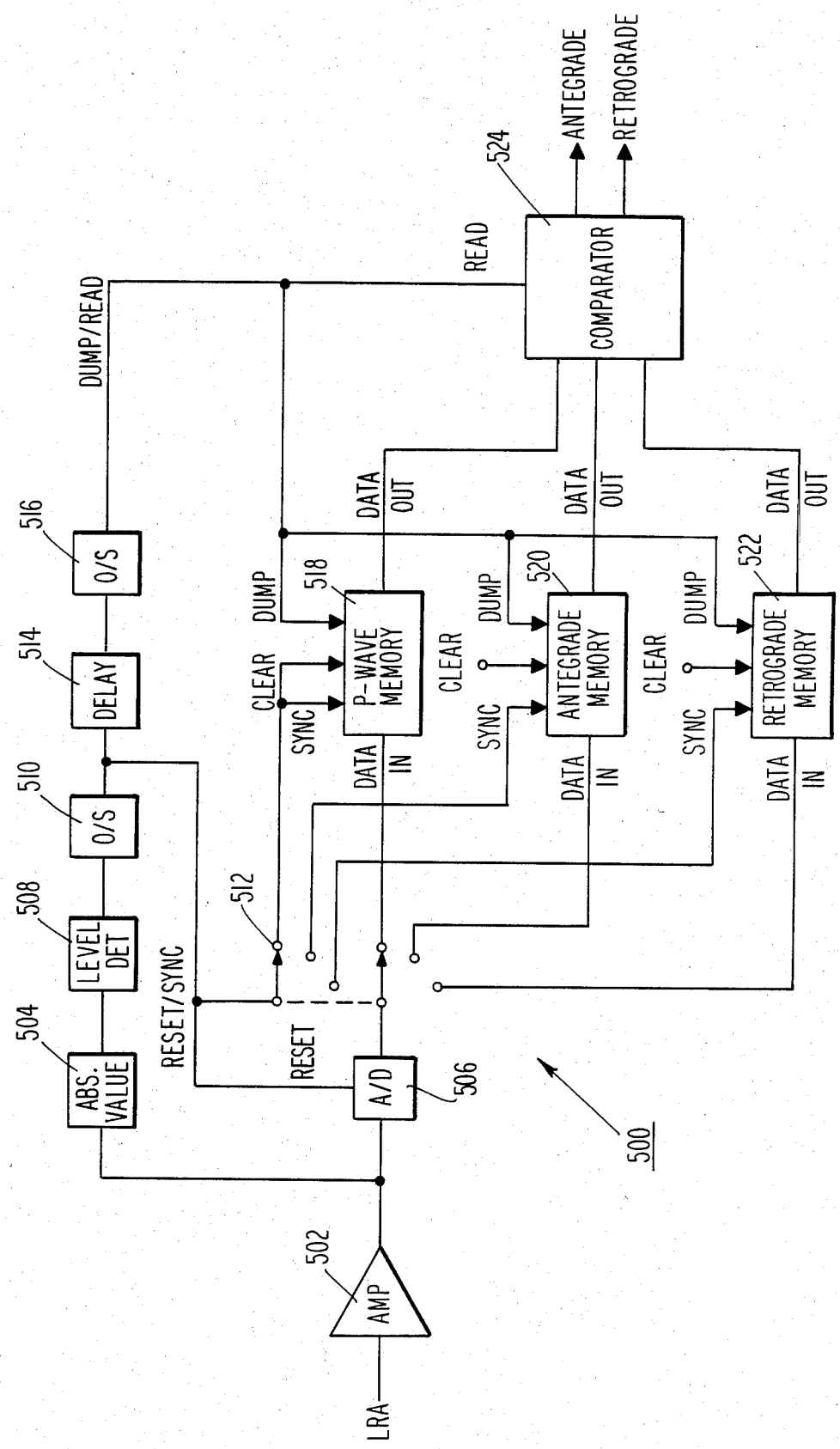
FIG. 6 is a block diagram depicting a P-wave morphology inversion detection circuit in accordance with the present invention.

Referring to FIG. 6, there is shown a circuit for detecting morphology inversion of the P-wave signals sensed at the LRA electrode. Morphology, as used herein, pertains to the shape as well as the polarity of the waveform. Consequently, a morphology inversion is substantially the mirror image of an uninverted waveform. This circuit, generally referred to as 500, comprises an amplifier 502 for receiving and amplifying the signals sensed at the LRA electrodes. In the preferred embodiment, the amplifier 502 incorporates band-pass filtering, amplifying those signals whose frequencies are in the range of 5–100 Hz in order to eliminate unwanted signal components such as base line shifts, T-waves, artifacts and noise. The output of amplifier 502 is connected to the input of an absolute value amplifier 504 and the input of an analog to digital converter 506. The absolute value amplifier 504 converts the amplified and filtered LRA waveform to a signal having a single polarity. This signal is connected to a level detector 508 which generates an output signal whenever the voltage of the input signal exceeds a predetermined level. The output of the level detector 508 is connected to the input of a first one shot 510.

The output of the first one shot 510 is connected to a reset input of the analog to digital converter 506, to a first pole of a two pole three position switch 512 and to the input of a delay circuit 514. The reset input of the analog to digital coverter 506 initializes the converter and enables it to receive analog data. The delay circuit 514 will output a pulse at a predetermined interval following the receipt of an input pulse. The output of the delay circuit 514 is connected to the input of a second one shot 516. The output of the second one shot 516 is connected to a dump input of a P-wave memory 518, a dump input of an antegrade memory 520, a dump input of a retrograde memory 522 and a read input of a digital comparator 524. The output of the analog to digital converter 506 is connected to a second pole of the two pole, three position switch 512. The first position of the second pole of switch 512 is connected to a data input of the P-wave memory 518. The second position of the second pole of switch 512 is connected to a data input of the antegrade memory 520. The third position of the second pole of switch 512 is connected to a data input of the retrograde memory 522.

The first position of the first pole of switch 512 is connected to a clear memory input of the P-wave memory 518. The second position of the first pole of switch 512 is connected to a sync input of the antegrade memory 520. The third position of the first pole of switch 512 is connected to a sync input of the retrograde memory 522. The data output of the P-wave memory 518 is connected to one input of the digital comparator 524. The data output of the antegrade memory 520 is connected to a second input of the comparator 524. The data output of the retrograde memory 522 is connected to a third input of the comparator 524.

The morphology inversion detection circuit 500 operates as follows. After filtering, amplification and shaping by the amplifier 502 and the absolute value amplifier 504, the LRA signal is applied to the input of the level detector 508. When this signal exceeds the predetermined reference voltage level, indicating the onset of a sensed P-wave, the level detector triggers the first one shot 510. The output of the first one shot 510, signalling the on-set of the P-wave, resets the analog to digital converter 506 and enables it to receive and digitize the analog data. In addition, the output of the first one shot 510 is applied to the input of the delay circuit 514 which starts the predetermined delay period. This delay period allows the analog to digital converter 506 time to receive and digitize the LRA signal from the amplifier 502 and transfer this digital data into one of the three memories, 518, 520 or 522.

The two pole three position switch 512 selects which of the three memories will receive the digital data from the analog to digital converter 506. In the first position, the first pole of switch 512 connects the output of the first one shot 510 to the clear memory input of the P-wave memory 518. A signal at the clear memory input clears the memory of the preceding data and enables it to receive digital information from the analog to digital converter 506. In the second and third positions, the first pole of switch 512 connects the output of the first one shot 510 to the sync inputs of the antegrade 520 and retrograde 522 memories respectively. The antegrade 520 and retrograde 522 memories are constructed to receive and store a preselected number, for example fifteen, digitized waveforms, average the stored waveforms, then store the average waveform which as a composite waveform represents the antegrade and retrograde waveforms which are present in that particular patient. Since the output of the first one shot 510 occurs at the on-set of each sensed P-wave, the antegrade 520 and retrograde 522 memories utilize the output of the first one shot 510 to the count and store the digitized P-wave data coming from the analog to digital converter 506. The first P-wave data will be stored in a first memory location; the second P-wave data will be stored in a second memory location; and so on until the preselected number, for example fifteen, waveforms have been received and stored at which time, the memory will stop receiving data and will calaculate and store the average composite waveform. Each of the antegrade 520 and retrograde 522 memories include a clear memory input which is useable by the operator to clear all memory locations prior to input of the average composite waveform data.

Initially, the operator will place switch 512 in the in the second position in order to read digital data representing the antegrade P-wave morphology into the antegrade memory 520 which provides the operator with a signal after receiving all data, and calculating and storing the average composite antegrade waveform data. Then, the operator will place switch 512 in the third position, induce retrograde P-wave conduction in the patient so that the digital information representing the retrograde P-wave morphology is read into the retrograde memory 522, which provides the operator with a signal after calculating and storing the average composite retrograde waveform data. Then, the induced retrograde P-wave conduction is terminated and the switch 512 is placed in its first position which enables the digital data representative of the signals sensed by the LRA electrodes to be read into the P-wave memory 518. Upon expiration of each predetermined delay period, the delay circuit 514 will output a pulse into the second one shot 516 which will generate a dump/read signal. This signal causes the digital information which is contained in the P-wave memory 518, as well as the average composite waveform data stored in the antegrade 520 and retrograde 522 memories to be read into the digital comparator 524.

The digital comparator 524 compares the data from the P-wave memory 518 with the average composite waveform data from the antegrade 520 and retrograde 522 memories, searching for a match between the digital data representing the LRA waveform and the previously stored data representing the morphology of the average composite antegrade waveform and the morphology of the average composite retrograde waveform. In the preferred embodiment, it is not necessary that there be a 100% correlation between compared morphologies. A correlation of 70% or greater is sufficient to provide an appropriate output from the comparator 524. If the comparator 524 detects an antegrade match, it will generate antegrade match output signal. If the comparator 524 detects a retrograde match, it will generate a retrograde match output signal. As preferably used in the pacemaker, an antegrade signal output from the comparator 524 is applied to the pacemaker A-V delay circuit which will trigger a ventricular pacing pulse if a spontaneous ventricular pulse is not detected within the predetermined delay period as previously described. A retrograde signal output from the comparator 524 is utilized by the pacemaker of the present invention to alleviate paroxysmal atrial tachycardia as will be subsequently described.

Referring now to FIG. 7, there is shown a block diagram of a paroxysmal atrial tachycardia (PAT) detection circuit, generally designated 600. The PAT detection circuit 600 comprises a rate detector 602 which receives the P-wave signal sensed by an atrial electrode. The rate detector 602 will output a signal if the rate of the input signal exceeds a predetermined reference rate, for example 150 beats per minute in the preferred embodiment. The output of the first rate detector 602 is applied to the input of a first one shot 604 through one input of a two input OR gate 606. A second rate detector 608 receives the ventricular pacing signal sensed by a ventricular electrode. The second rate detector 608 generates a pulse upon detection of an input signal having a rate which exceeds a predetermined reference rate, for example 150 beats per minute in the preferred embodiment. The output of the second rate detector 608 is connected to the input of the first one shot 604 through the other input of the two input OR gate 606.

A pulse width detector 610 receives an electrocardiogram signal at its input. In the preferred embodiment, this electrocardiogram signal is obtained using skin sensors as is known in the art or from the RV electrode referenced to the skin at the location of the pacemaker housing. The pulse width detector 610 generates an output pulse when the width of the QRS signal portion of the electrocardiogram is less than a predetermined duration, for example one hundred twenty milliseconds in the preferred embodiment.

The output of the pulse width detector 610 is connected to the input of a second one shot 612. The output of the second one shot 612 is applied to the input of a switch 614 which is opened and closed by means of a programmable control. The second (retrograde) trigger output of the sequence detector circuit 400 is connected to the input of a third one shot 616. As shown in FIG. 7, as an alternate embodiment, the P-wave morphology inversion detection circuit 500 may be used instead of the sequence detection circuit 400 with the retrograde signal output of the digital comparator 524 being connected to the input of the third one shot 616. In either case, the third one shot 616 will receive an input pulse upon detection of a retrograde P-wave in the atrium. Upon receipt of such signal, the third one shot 616 generates an output pulse of predetermined duration, for example one hundred fifty milliseconds in the preferred embodiment, which is applied to an input of a three input AND gate 618.

The first one shot 604 will generate a pulse of predetermined width, for example one hundred fifty milliseconds in the preferred embodiment, upon receipt of an input signal from the OR gate 606. The output pulse from the first one shot 604 is applied to a second input of the three input AND gate 618. The third one shot 612 generates an output pulse of predetermined width, for example one hundred fifty milliseconds in the preferred embodiment, upon receipt of an input pulse from the pulse width detector 610. The output pulse from the second one shot 612 is applied to a third input of the three input AND gate 618 whenever the switch 614 is closed by the user operating the programmable control. Upon coincidence of the inputs from the first 604, second 612 and third 616 one shots, the three input AND gate 618 will generate an output signal.

The PAT detection circuit 600 operates as follows. Upon detection of atrial pacing pulses which exceed a rate of 150 beats per minute in the preferred embodiment, the first rate detector 602 will provide a pulse to the first one shot 604 through the OR gate 606, causing the first one shot 604 to provide an output pulse for a predetermined duration. Alternatively, upon detection of ventricular pacing pulses which exceed the predetermined rate of 150 beats per minute, the second rate detector 608 generates a pulse which is applied to the input of the first one shot 604 through the other input of the two input OR gate 606, which also causes the first one shot 604 to output a pulse for the predetermined time period. As previously stated, the output pulse from the first one shot 604 is applied to an input of the three input AND gate 618.

Upon detection of a QRS pulse width which is less than one hundred twenty milliseconds in the preferred embodiment, the pulse width detector 610 applies an input pulse to the second one shot 612. Assuming that the operator has closed switch 614, the output of the second one shot 612, which is a pulse having a duration of one hundred fifty milliseconds, is applied to a second input of the three input AND gate 618. As previously described in detail, upon detection of an LRA signal occuring before the detection of an HRA signal, the sequence detector 400 will generate a second (retrograde) trigger signal. This retrograde trigger signal is applied to the input of the third one shot 616 which then generates an output pulse having a duration of one hundred fifty milliseconds. As previously stated, the morphology inversion detection circuit 500 can be used instead of the sequence detection circuit 400. In such case, upon detection of an inversion of the morphology of the LRA signal, the inversion detection circuit will generate a retrograde signal which is applied to the input of the third one shot 616. The output pulse of the third one shot 616 is applied to the third input of the three input AND gate 618.

The AND gate 618 will generate an output signal upon coincidence of the output pulses from the first 604, second 612 and third 616 one shots. This output is indicative of the detection of an atrial or ventricular pacing rate which exceeds one hundred fifty beats per minute in conjunction with a QRS complex having a duration of less than one hundred milliseconds and the detection of retrograde P-waves in the atrium. It has been found that high rate atrial beats or high rate ventricular beats (in excess of approximately 150 beats per minutes), in conjunction with the presence of retrograde P-waves on a 1:1 basis (that is, the high rate atrial beat results from retrograde P-wave conduction emanating from the A-V node) and a narrow QRS complex (preferably less than one hundred milliseconds) uniquely determines the existence of paroxysmal atrial tachycardia (PAT) which can be alleviated by applying either premature atrial pacing pulses or a burst of high rate atrial pacing pulses. Consequently, the output signal from the AND gate 618 will be used by the improved pacemaker of the present invention to generate premature atrial pacing pulses or a burst of high rate atrial pacing pulses to alleviate PAT.

In some patients, especially those having right or left bundle branch block, PAT can occur in spite of QRS complexes having widths which exceed one hundred milliseconds. In patients exhibiting this phenomena, switch 614 is operated to open the circuit from the second one shot 612 to the input terminal of the AND gate 618 and to apply a constant coincidence signal to the input terminal thereby eliminating the necessity of coincidence of narrow (preferably less than one hundred milliseconds) QRS pulses in order to generate an output signal from the AND gate 618. In these patients, PAT is determined by the coincidence of high rate atrial and/or ventricular pacing pulses and 1:1 retrograde P-waves.

As seen from the previous description, a pacemaker employing the present invention is able to differentiate between antegrade and retrograde P-waves and ignore retrograde P-waves. It will generate a ventricular pacing pulse only after recognition of an antegrade P-wave; consequently, the heart will not be driven into tachycardia which results when the delayed ventricular pacing pulse is triggered by a retrograde P-wave. Prior art attempts to prevent pacemaker mediated tachycardia have included employing an atrial amplifier refractory clamp and/or an upper pacing rate limit, for example 120 beats per minute, which rate would not be exceeded by the pacemaker. In this way, the pacemaker generates a ventricular pacing pulse at the maximum rate of one every 500 milliseconds regardless of the frequency of sensed P-waves in the atrium.

The problem is that this type pacemaker is unable to track the natural physiological response to the sinus node, which, as a result of heavy physical activity, could trigger P-waves at the rate of 160 beats per minute or higher, depending upon the intensity of the physical activity. The prior art pacemakers do not always provide a true physiologic response for an individual participating in strenuous physical activity. The improved pacemaker in accordance with the present invention can, by differentiating between antegrade P-waves and retrograde P-waves, truely track the physiological response since it does not require an atrial amplifier refractory clamp or an upper allowable pacing limit to prevent pacemaker mediated tachycardia.

While the principles of the present invention have now been made clear in an illustrative embodiment, there will be immediately obvious to those skilled in the art many modifications of structure, arrangement, the elements, material and components used in the practice of the invention and otherwise, which are particularly adapted for specific environments and operating requirements without departing from those principles. For example, the detection of timing sequence of the HRA signal with respect to the LRA signal can be performed using digital techniques which measure, calculate and store average composite antegrade and retrograde HRA/LRA detection times occurring in a particular patient. This information is then used to indicate antegrade or retrograde P-wave conduction based on sequence of occurrence and interval time data uniquely associated with that patient. The appended claims are, therefore, intended to cover and embrace any such modifications within the limits only of the true spirit and scope of the invention.

I claim:

1. A method for detecting retrograde P-wave conduction from an A-V node through an atrium of a human heart, said method comprising the steps of:
   (a) sensing a P-wave signal at a first location in said atrium;
   (b) sensing said P-wave signal at a second location in said atrium, said second location being intermediate said first location and said A-V node;
   (c) comparing the time at which said P-wave is sensed at said first location with the time at which said P-wave is sensed at said second location; and
   (d) indicating the occurrence of a retrograde P-wave whenever said P-wave is sensed at said second location before it is sensed at said first location.

2. A method in accordance with claim 1 wherein step a comprises:
   (1) placing a bipolar electrode pair within said atrium in proximity to a sinus node; and
   (2) detecting the occurrence of an electrical P-wave signal acquired by said bipolar electrode pair.

3. A method in accordance with claim 1 wherein step b comprises:
   (1) placing a bipolar electrode pair in said atrium in proximity to a valve disposed between said atrium and said ventricle, on the atrial side of said valve in proximity to said A-V node; and
   (2) detecting the occurrence of an electrical P-wave signal acquired by said bipolar electrode pair.

4. A method in accordance with claim 1 wherein step a comprises:
   (1) placing a unipolar electrode within said atrium in proximity to a sinus node; and
   (2) detecting the occurrence of an electrical P-wave signal acquired by said unipolar electrode.

5. A method in accordance with claim 1 wherein step b comprises:
   (1) placing a unipolar electrode adjacent the wall of said atrium in proximity to a valve disposed between said atrium and said ventricle, on the atrial side of said valve in proximity to said A-V node; and
   (2) detecting the occurrence of an electrical P-wave signal acquired by said unipolar electrode.

6. An apparatus for detecting retrograde P-wave conduction from an A-V node through an atrium of a human heart, said apparatus comprising:
   (a) means for sensing a P-wave signal at a first location in said atrium;
   (b) means for sensing said P-wave signal at a second location in said atrium, said second location being intermediate said first location and said A-V node;
   (c) means for comparing the time at which said P-wave is sensed at said first location with the time at which said P-wave is sensed at said second location; and
   (d) means for indicating the occurrence of a retrograde P-wave whenever said P-wave is sensed at said second location before it is sensed at said first location.

7. An apparatus in accordance with claim 6 wherein said first location sensing means comprises a bipolar electrode pair positioned within said atrium in proximity to a sinus node.

8. An apparatus in accordance with claim 6 wherein said second location sensing means comprises a bipolar electrode positioned in said atrium in proximity to a valve disposed between said atrium and said ventricle, on the atrial side of said valve in proximity to said A-V node.

9. An apparatus in accordance with claim 6 wherein said first location sensing means comprises a unipolar electrode positioned within said atrium in proximity to a sinus node.

10. An apparatus in accordance with claim 6 wherein said second location sensing means comprises a unipolar electrode positioned in said atrium in proximity to the valve disposed between said atrium and said ventricle, on the atrial side of said valve in proximity to said A-V node.

11. A method for inhibiting tachycardia initiated by a pacemaker having means for sensing the occurrence of a P-wave within an atrium of a human heart and means for generating a pacing pulse to a ventricle of said heart at a predetermined time following the occurrence of said P-wave, said method comprising the steps of:
    (a) sensing the occurrence of said P-wave at a first location in said atrium;
    (b) sensing the occurrence of said P-wave at a second location in said atrium, said second location being intermediate said first location and said ventricle;
    (c) comparing the time at which said P-wave occurs at said first location with the time at which said P-wave occurs at said second location; and
    (d) inhibiting the generation of said ventricular pacing pulse whenever said P-wave occurs at said second location before it occurs at said first location.

12. A method in accordance with claim 11 additionally comprising the step of:
    (e) generating said ventricular pacing pulse whenever said P-wave occurs at said first location before it occurs at said second location.

13. A method in accordance with claims 11 or 12 wherein step a comprises:
    (1) placing a bipolar electrode pair within said atrium in proximity to a sinus node; and
    (2) detecting the occurrence of an electrical P-wave signal acquired by said bipolar electrode pair.

14. A method in accordance with claims 11 or 12 wherein step b comprises:
    (1) placing a bipolar electrode pair in said atrium in proximity to a valve disposed between said atrium and said ventricle, on the atrial side of said valve in proximity to said A-V node; and
    (2) detecting the occurrence of an electrical P-wave signal acquired by said bipolar electrode pair.

15. A method in accordance with claims 11 or 12 wherein step a comprises:
    (1) placing a unipolar electrode within said atrium in proximity to a sinus node; and (2) detecting the occurrence of an electrical P-wave signal acquired by said unipolar electrode.

16. A method in accordance with claims 11 or 12 wherein step b comprises:
   (1) placing a unipolar electrode adjacent the wall of said atrium in proximity to the valve disposed between said atrium and said ventricle, on the atrial side of said valve in proximity to said A-V node; and
   (2) detecting the occurrence of an electrical P-wave signal acquired by said unipolar electrode.

17. In a cardiac pacemaker including means for sensing occurrence of a P-wave within an atrium of a human heart and means for generating pacing pulse to a ventricle of said heart at a predetermined time following the occurrence of said P-wave; an improvement for inhibiting tachycardia initiated by said pacemaker, said improvement comprising:
   (a) means for sensing the occurrrence of said P-wave at a first location in said atrium;
   (b) means for sensing the occurrence of said P-wave at a second location in said atrium, said second location being intermediate said first location and said ventricle;
   (c) means for comparing the time at which said P-wave occurs at said first location with the time at which said P-wave occurs at said second location; and
   (d) means for inhibiting the generation of said ventricular pacing pulse whenever said P-wave occurs at said second location before it occurs at said first location.

18. The improvement in accordance with claim 17 wherein said second location sensing means comprises a bipolar electrode pair positioned in said atrium in proximity to a valve disposed between said atrium and said ventricle, on the atrial side of said valve in proximity to said A-V node.

19. The improvement in accordance with claim 17 wherein said first location sensing means comprises a unipolar electrode positioned within said atrium in proximity to a sinus node.

20. The improvement in accordance with claim 17 additionally comprising:
   (e) means for enabling the generation of said ventricular pacing pulse whenever said P-wave occurs at said first location before it occurs at said second location.

21. The improvement in accordance with claims 17 or 20 wherein said first location sensing means comprises a bipolar electrode pair positioned within said atrium in proximity to a sinus node.

22. The improvement in accordance with claims 17 or 20 wherein said second location sensing means comprises a unipolar electrode positioned in said atrium in proximity to the valve disposed between said atrium and said ventricle, on the atrial side of said valve in proximity to said A-V node.

23. An apparatus for differentiating between retrograde P-wave conduction from an A-V node through an atrium of a heart and antegrade P-wave conduction through said atrium, said apparatus comprising:
   (a) first means for sensing the occurrence of a P-wave, said first means adapted to be operatively connected to the heart at a first location on or in the atrium;
   (b) second means for sensing the occurrence of said P-wave, said second means adapted to be operatively connected to the heart at a second location on or in the atrium, said second location being intermediate said first location and said A-V node;
   (c) means, responsive to said first and second P-wave sensing means, for comparing the time of occurrence of said P-wave at said first location with the time of occurrence of said P-wave at said second location; and
   (d) means for providing a signal indicating the occurrence of a retrograde P-wave whenever said P-wave is sensed at said second location before it is sensed at said first location.

24. An apparatus in accordance with claim 23 additionally comprising:
   (e) means for providing a second signal indicating the occurrence of an antegrade P-wave whenever said P-wave is sensed at said first location before it is sensed at said second location.

25. An apparatus in accordance with claims 23 or 24 wherein said first P-wave sensing means comprises a unipolar electrode adapted to be operatively connected to the heart on or in the atrium in proximity to a sinus node.

26. An apparatus in accordance with claim 25 wherein said second P-wave sensing means comprises a unipolar electrode adapted to be operatively connected to the heart on or in the atrium in proximity to a valve disposed between said atrium and said ventricle, on the atrial side of said valve in proximity to said A-V node.

27. An apparatus in accordance with claims 23 or 24 wherein said first P-wave sensing means comprises a bi-polar electrode pair operatively connected to the heart on or in the atrium in proximity to a sinus node.

28. An apparatus in accordance with claim 27 wherein said second P-wave sensing means comprises a bi-polar electrode adapted to be operatively connected to the heart on or in the atrium in proximity to a valve disposed between said atrium and said ventricle, on the atrial side of said valve in proximity to said A-V node.

29. A cardiac pacemaker including first means for sensing the occurrence of a P-wave in an atrium of a heart, said first means adapted to be operatively connected to the heart at a first location on or in the atrium, and means for generating a pacing pulse at a predetermined time following the occurrence of said P-wave, said pacing pulse generating means adapted to be operatively connected to the heart on or in the ventricle thereof, said improvement comprising:
   (a) second means for sensing the occurrence of said P-wave, said second means adapted to be operatively connected to the heart at a second location on or in the atrium, said second location being intermediate said first location and an A-V node;
   (b) means, responsive to said first and second P-wave sensing means, for comparing the time of occurrence of said P-wave at said first location with the time of occurrence of said P-wave at said second location;
   (c) means for inhibiting the generation of said ventricular pacing pulse whenever said P-wave occurs at said second location before it occurs at said first location; and
   (d) means for enabling the generation of said ventricular pacing pulse whenever said P-wave occurs at said first location before it occurs at said second location.

30. The improvement in accordance with claim 29 wherein said first P-wave sensing means comprises a bi-polar electrode pair adapted to be operatively connected to the heart on or in the atrium in proximity to a sinus node.

31. The improvement in accordance with claim 30 wherein said second P-wave sensing means comprises a bi-polar electrode pair adapted to be operatively connected to the heart on or in the atrium in proximity to a valve disposed between said atrium and said ventricle, on the atrial side of said valve in proximity to said A-V node.

32. The improvement in accordance with claim 29 wherein said first P-wave sensing means comprises a unipolar electrode adapted to be operatively connected to the heart on or in the atrium in proximity to a sinus node.

33. The improvement in accordance with claim 32 wherein said second P-wave sensing means comprises a unipolar electrode adapted to be operatively connected to the heart on or in the atrium in proximity to a valve disposed between said atrium and said ventricle, on the atrial side of said valve in proximity to said A-V node.

* * * * *